United States Patent
Field

(10) Patent No.: US 6,593,140 B1
(45) Date of Patent: Jul. 15, 2003

(54) ANIMAL CELL CULTURE

(75) Inventor: Raymond Paul Field, Congleton (GB)

(73) Assignee: Lonza Group, AG, Zürich (CH)

( * ) Notice: Subject to any disclaimer, the term of this patent is extended or adjusted under 35 U.S.C. 154(b) by 0 days.

(21) Appl. No.: 08/418,930

(22) PCT Filed: Jul. 26, 1993

(86) PCT No.: PCT/GB93/01572

§ 371 (c)(1),
(2), (4) Date: Mar. 24, 1994

(87) PCT Pub. No.: WO94/02592

PCT Pub. Date: Feb. 3, 1994

Related U.S. Application Data

(63) Continuation of application No. 08/211,344, filed on Mar. 24, 1994, now abandoned.

(30) Foreign Application Priority Data

Jul. 24, 1992 (GB) ............................................ 9215834

(51) Int. Cl.$^7$ .................................................. C12N 5/00
(52) U.S. Cl. ...................... 435/404; 435/325; 435/405
(58) Field of Search .................. 435/240.2, 240.21, 435/240.3, 240.31, 325, 404, 405; 514/279

(56) References Cited

U.S. PATENT DOCUMENTS 4,816,401 A    3/1989   Taupier et al.

FOREIGN PATENT DOCUMENTS

| EP | 0 256 055 | 2/1988 |
| EP | 0 274 445 | 7/1988 |
| WO | WO87/00195 | 1/1987 |
| WO | WO90/03430 | 4/1990 |

OTHER PUBLICATIONS

Montoni, Boll. Soc. Ital. Biol. Sper (Italy) 43 (1) p 14–17 (Jan. 15, 1967).*
Inamori et al, Biol. Pharm Bull (Japan), 16(5), p 521–523 (May 1993).*
White et al, Blood, 48(6) p 923–929 (1976).*
Forsbeck et al, Eur. J. Haemotol., 39(4) p 318–25 (1987).*
Forsbeck et al., "Variation in Iron Accumulation, Transferrin Membrane Binding and DNA Synthesis in the K–562 and U–937 Cell Lines Induced by Chelators and Their Iron Complexes," Medline Abstract No. 88083462, Eur J. Haematol 39 (4) 318–25 (Oct. 1987).
C.R. Bebbington et al., "High–Level Expression of a Recombinant Antibody from Myeloma Cells Using a Glutatime Synthetase Gene as an Amplifiable Selectable Marker", Bio/Technology, vol. 10, 169–175 (Feb. 1992).
Murakami et al., "Growth of Hybridoma Cells in Serum–Free Medium: Ethanolamine is an Essential Component," Proc.Natl.Acad.Sci. USA, vol. 79, pp. 1158–1162, (Feb. 1982).
Darfler et al., "Serum–Free Culture of Resting, PHA–Stimulated, and Transformed Lymphoid Cells, Including Hybridomas", Experimental Cell Research, vol. 138, pp. 287–295 (1982).
van Wezel, "The Large–Scale Cultivation of Diploid Cell Strains in Microcarrier Culture. Improvement of Microcarriers," Develop.biol.Standard, vol. 37, pp. 143–147 (1977).
Crespi et al., "Continuous Cell Propagation Using Low–Charge Microcarriers," Biotechnology and Bioengineering vol. XXIII, pp. 983–993 (1981).
Hu et al., "A Mechanistic Analysis of the Inoculum Requirement for the Cultivation of Mammalian Cells on Microcarriers," Biotechnology and Bioengineering, vol. XXVII, pp. 585–595 (1985).
Forsbeck et al., "Variation in Iron Accumulation, Transferrin Membrane Binding and DNA Synthesis in the K–562 and U–937 Cell Lines Induced by Chelators and Their Iron Complexes", File Server STN Karlsruhe, File Medlin Abstract No. 88083462, 39(4), pp. 318–325, (Oct. 1987).

* cited by examiner

*Primary Examiner*—Leon B. Lankford, Jr.
(74) *Attorney, Agent, or Firm*—Venable; Marina V. Schneller

(57) ABSTRACT

An animal cell culture medium is described which contains 2-hydroxy-2,4,6-cycloheptatrien-1-one or a derivative thereof to support the growth of animal cells, particularly in agitated cell culture at low iron concentrations.

14 Claims, 5 Drawing Sheets

SPARGED FERMENTATIONS OF THE SAME
HYBRIDOMA CELL LINE IN EITHER PROTEIN-FREE
MEDIUM WITH TROPOLONE OR MEDIUM
CONTAINING TRANSFERRIN

PROTEIN-FREE MEDIUM CONTAINING TROPOLONE

MEDIUM CONTAINING TRANSFERRIN

ANIMAL CELL CULTURE

This application is a continuation of application Ser. No. 08/211,344, filed Mar. 24, 1994 now abandoned.

FIELD OF THE INVENTION

This invention relates to improvements in animal cell culture, particularly to improvements in methods for growing animal cells and nutrient media therefor.

BACKGROUND TO THE INVENTION

The use of animal cell culture for the mass production of cell products such as immunoglobulins, hormones and enzymes is becoming increasingly important from a commercial point of view, and currently there is considerable effort devoted to the development of cell culture techniques for the optimisation of the large scale production of these materials.

Animal cells in culture require a basal nutrient mixture of salts, sugars, amino acids and vitamins. Usually the mixture is supplemented with a biological fluid or extract, in the absence of which most cells lose viability or fail to proliferate. The most commonly used supplement is serum.

The use of supplements, however, is not very satisfactory, since their generally undefined nature, and the variations that can exist between batches of a given type, can affect the success and reproducibility of a culture. There have thus been numerous attempts to identify the active factors in supplements such as serum, with a view to providing a better defined medium to support the growth of cells in culture. To date, this approach has met with limited success, largely due to the complex nature of biological supplements and the very small amounts of active factors that they contain.

A number of supplement-free media have been described, however, some of which are available commercially [see for example Murakami et al, Proc. Natl. Acad. Sci. USA 79, 1158–1162 (1982); Darfler et al., Exp. Cell Res. 138, 287–295 (1982) and International Patent Specification No. WO 90/03430].

Supplement-free media generally contain a complex mixture of amino acids, salts, vitamins, trace elements, carbohydrates and other growth supporting components such as albumin, insulin, glutamine, transferrin, ferritin and ethanolamine [see for example U.S. Pat. No. 4,816,401]. When cultured in such media, animal cells remain viable for a finite period of time, until one or more essential nutrients in the medium become exhausted. At such time the medium may be supplemented with a feed containing one or more energy sources and one or more amino acids [see for example International Patent Specification No. WO 87/00195]. In this way the culture may be prolonged to increase yield of cells or cell products.

Metal ions, especially ferrous and ferric ions, are essential for animal cell metabolism, and are present in culture media as components of undefined supplements such as serum, or as components of salts and trace elements included in supplement-free media. Cellular demand for metal ions can become high in animal cell culture, especially when high cell densities are reached and in practice this means that metal ions need to be made continuously available in culture to support the growth and viability of cells. To achieve this in a supplement-free medium high concentrations of a simple salt of the metal can be used, but it is often necessary for the metal to be in a chelated form in the medium to facilitate cellular uptake of the metal and/or to avoid the solubility and toxicity problems which can be associated with high metal ion concentrations.

To supply sufficient iron to cells growing in supplement-free media, simple or complex iron salts such as ferrous sulphate, ferric chloride, ferric nitrate or ferric ammonium citrate have been used, where necessary often in combination with a chelating agent. Particular iron chelating agents which have been used in cell culture include the natural proteins transferrin and ferritin; organic acids such as citric acid, iminodiacetic acid and gluconic acid; pyridoxal isonicotinoyl hydrazone; and aurin tricarboxylic acid.

A number of factors are important in selecting an iron chelating agent for general use in supplement-free media for animal cell culture. Thus, the chelating agent must have an appropriate binding affinity for the iron and be able to transport it efficiently across the cell membrane. It must also be cheap, readily available and non-toxic. Increasingly importantly, the chelating agent should be of synthetic, not animal, origin to avoid any possible unwanted contamination of any desired cell product and a consequent increase in the cost of recovery of a pure product. None of the above-mentioned chelating agents meets all of these criteria.

SUMMARY OF THE INVENTION

We have now found that 2-hydroxy-2,4,6-cycloheptatrien-1-one meets all of these criteria and may be used advantageously in animal cell culture to support the growth of cells. In particular, we have found that its use can support growth in agitated cell culture, where it is necessary to use low iron concentration to avoid toxicity problems, and where the use of other recognised chelating agents such as citrate and gluconate has failed. We have used this discovery to develop a medium and a process for the growth of animal cells.

Thus, according to one aspect of the invention, we provide a nutrient animal cell culture medium comprising assimilable sources of carbon, nitrogen, amino acids, iron and other inorganic ions, trace elements and optionally lipids and growth promoters or regulators in admixture with 2-hydroxy-2,4,6-cycloheptatrien-1-one or a derivative thereof.

DETAILED DESCRIPTION OF THE INVENTION

In general the nutrient medium may be any known basal medium or variants thereof which will support the continuous growth of animal cells and/or sustain them during a stationary phase, to which 2-hydroxy-2,4,6-cycloheptatrien-1-one [hereinafter sometimes referred to as tropolone] or a derivative thereof has been added. Known basal media and variants thereof include for example Dulbecco's Modification of Eagle's Medium (DMEM), Iscove Modified Dulbecco's Medium, Ham's Medium, Roswell Park Memorial Institute Medium (RPMI) and Fischer's Medium, or those described by Hu et al. in Biotechnol. Bioeng. (1985), 27, 585–595; by Crespi and Thilly in Biotechnol. Bioeng. (1981), 23, 983–993, and by Van Wezel in Dev. Biol. Stand. (1977), 37, 143–147. In one preferred aspect, the medium is a protein-free medium.

The tropolone or derivative thereof is generally present in the medium according to the invention at a concentration sufficient to support the growth and viability of the cells. The exact concentration may vary depending on the cell line in use and the other media components present, but may be easily determined using preliminary small scale tests in accordance with conventional practice. Thus, for example, for any chosen medium cells may be cultured on a small scale in the presence of a range of tropolone concentrations and the optimum concentration determined by observing the effect of different concentrations on cell growth and viability.

In general, the tropolone or tropolone derivative will be present in an excess molar concentration to the iron present in the medium for example at a molar ratio of around 5 to 1 to around 70 to 1, for example around 10 to 1 to around 70 to 1. Thus for example where the iron concentration in the medium is around 0.3 $\mu$M, the tropolone or derivative thereof may be employed at a concentration of around 1.5 $\mu$M to around 20 $\mu$M, e.g. around 3 $\mu$M to around 20 $\mu$M. The iron may be present as ferrous or ferric ions, for example resulting from the use of simple or complex iron salts in the medium such as ferrous sulphate, ferric chloride, ferric nitrate or in particular ferric ammonium citrate.

Tropolone derivatives for use in the media according to the invention in general are those derivatives which are capable of chelating ferrous or ferric ions. Particular derivatives include those wherein one or more ring carbon atoms of tropolone are substituted by aliphatic, aromatic or heteroaromatic groups, e.g. by alkyl, alkenyl, alkynyl, aryl, aralkyl, aralkenyl, aralkynyl, heteroaryl, heteroaralkyl, heteroaralkenyl or heteroaralkynyl groups. Tropolone or derivatives thereof are either commercially available [e.g. from the Aldrich Chemical Co.] or may be prepared using known literature procedures.

The media according to the invention may be prepared by appropriate mixture of individual components using conventional procedures and may either be provided in liquid form, or in dry form for reconstitution before use with an appropriate buffer, e.g. a bicarbonate buffer. In preparing the media according to the invention, it is advisable to avoid the use of a concentrated liquid mixture of tropolone and iron.

The media according to the invention may be used to culture animal cells. Thus according to a further aspect of the invention we provide a nutrient animal cell culture medium comprising assimilable sources of carbon, nitrogen, amino acids, iron and other inorganic ions, trace elements and optionally lipids and growth promoters or regulators in admixture with 2-hydroxy-2,4,6-cycloheptatrien-1-one or a derivative thereof for the continuous growth of animal cells.

The media according to the invention are particularly suitable for the continuous growth of animal cells in an agitated culture, particularly at a low iron concentration, e.g. at an iron concentration of around 0.3 $\mu$M.

The animal cells which may be cultured according to the invention may be for example genetically engineered cells, lymphoid cells e.g. myeloma cells, or hybridoma or other fused cells. Particular cell types include cells of human, rat, mouse or hamster origin. The medium according to the invention is particularly suitable for use with lymphoid cells, especially myeloma cells, particularly of mouse origin, especially NS/O cells.

The media according to the invention may be used to culture animal cells to obtain an animal cell product. Thus according to a further aspect of the invention, we provide a process for obtaining an animal cell product by cell culture which comprises the steps of (1) culturing animal cells which produce said product in a nutrient culture medium comprising assimilable sources of carbon, nitrogen, amino acids, iron and other inorganic ions, trace elements and optionally lipids and growth promoters or regulators in admixture with 2-hydroxy-2,4,6-cycloheptatrien-1-one or a derivative thereof, (2) continuing the culture until said product accumulates and (3) recovering said product.

Cell products which may be obtained according to the invention include any products which are produced by cultured animal cells. Typical products include polypeptides and proteins, for example immunoglobulins such as monoclonal and recombinant antibodies and fragments thereof, hormones such as erythropoietin and growth hormone, e.g. human growth hormone, lymphokines such as interferon, interleukins such as interleukin 2, 4, 5 and 6 and industrially and therapeutically useful enzymes such as tissue plasminogen activator.

In the process according to the invention, the animal cells may generally be cultured in suspension in the culture medium in a suitable culture vessel, for example a stirred tank or airlift fermenter, using known culture techniques.

Thus, for example, a seed culture of suitable cells, obtained by conventional techniques, may be used to inoculate the culture medium. In general, the number of cells used for inoculation will be in the range $1 \times 10^5$ to $5 \times 10^5$ cells ml$^{-1}$ or less. The cells are then cultured until a desired cell density is reached and/or until sufficient product has accumulated.

The production of the desired products during the culture may be monitored using any appropriate assay for the particular product in question. Thus, for example, where the product is a polypeptide or protein, the production of this may be monitored by general assay techniques such as enzyme-linked immunoabsorbent assay or immunoradiometric assay adapted for use with the particular polypeptide or protein.

Where in the process according to the invention it is desired to isolate the cell product obtained, this may be achieved using conventional separation and purification techniques. Thus, for example, where the product is secreted by the cells into the medium it may be separated from the cells using techniques such as centrifugation and filtration and then further purified using, for example, affinity purification techniques, such as affinity chromatography. Where the product is not secreted by the cells, the above methods may still be used, but after the cells have first been lysed to release the product.

BRIEF DESCRIPTION OF THE DRAWINGS

The invention is now described by way of illustration only in the following Examples which refer to the accompanying diagrams in which.

DESCRIPTION OF SPECIFIC EMBODIMENTS

The following Examples illustrate the invention.

EXAMPLE 1

A mouse hybridoma cell line previously subcultured in a serum-free medium containing 1 $\mu$g/ml human transferrin was centrifuged and resuspended in transferrin-free medium twice. Cells were finally resuspended at a density of $1.5 \times 10^5$ cells/ml in transferrin-free growth medium containing 0.1 mg/l ferric ammonium citrate.

100×concentrates of the iron chelators to be tested (8-hydroxyquinoline, tropolone, mimosine, maltol or picolinic acid) were prepared in water and filter sterilised. 10 $\mu$l of each iron chelator was dispersed into wells of a 24 well costar plate and then 1 ml of cell suspension added.

Acetylacetone was prepared as a 0.05 M stock in ethanol and 2 $\mu$l was dispersed into tissue culture wells, followed by 1 ml of cell suspension. Control wells contained either 10 μl water (negative control) or 10 μl of 100 μg/ml human transferrin solution (positive control).

Plates were incubated for 3 days in a humidified incubator under a 5% $CO_2$—95% air atmosphere at 36.5° C. under static conditions.

After 3 days samples of dispersed cell suspensions from individual wells were analysed using a Coulter Multisizer to determine cell concentration.

Figure 1A:
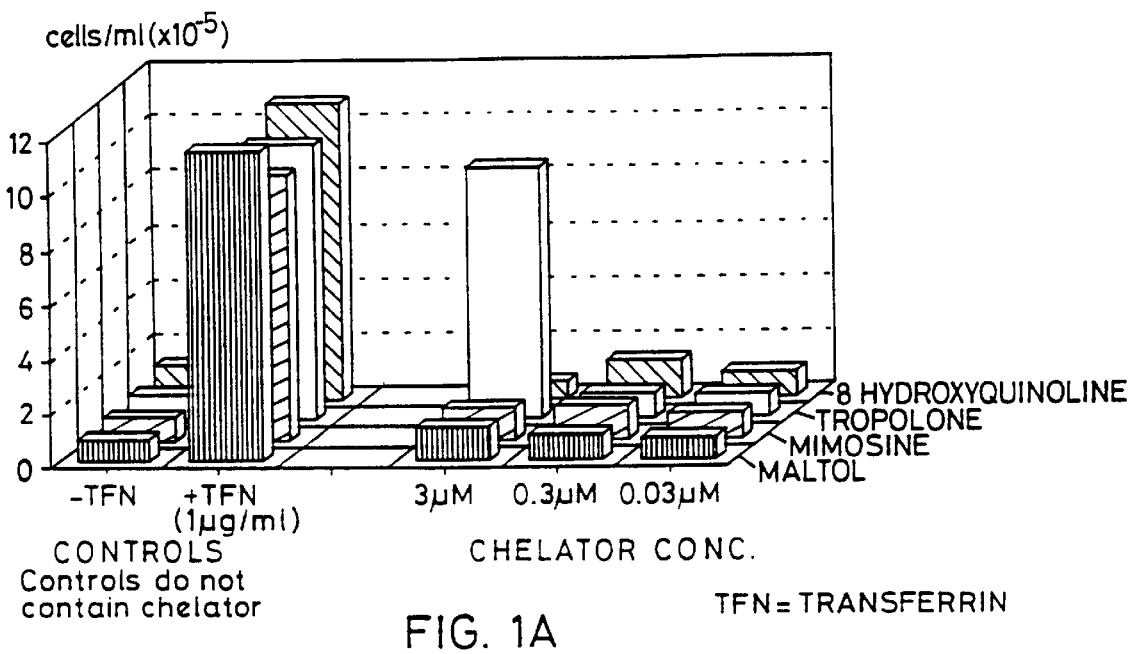
FIGS. 1–3 show the growth of mouse hybridoma cells in the presence of tropolone and various other chelators.

FIG. 1A shows 3 μM tropolone to be as effective as 1 μg/ml of human transferrin at supporting cell growth in the presence of 0.36 μM iron (=0.1 mg/l ferric ammonium citrate). Other lipophilic chelators at concentrations of 0.03–3 μM did not support growth of cells in the absence of transferrin.

Figure 1B:
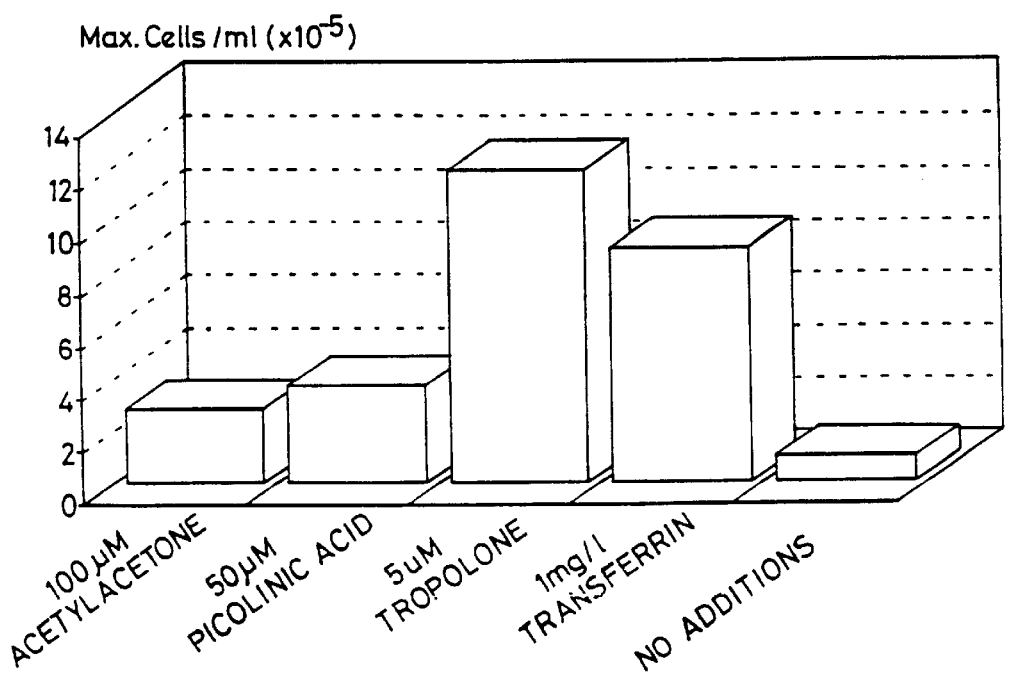

FIG. 1B shows 5 μM tropolone to be effective at supporting cell growth, whereas 100 μM acetylacetone and 50 μM picolinic acid were much less effective. These concentrations of picolinic acid and acetylacetone were chosen as the optimum from a previous experiment (data not shown).

All media contained 0.1 mg/l ferric ammonium citrate.

EXAMPLE 2

Methods

A mouse hybridoma cell line, previously subcultured in serum free medium containing human transferrin, was centrifuged and resuspended at $1.5 \times 10^5$ cells/ml in either transferrin-free or transferrin-containing serum-free medium. All media contained 0.1, 1, or 10 mg/l of added ferric ammonium citrate. The flasks were gassed in 5% $CO_2$—95% air atmosphere, sealed and incubated either static or on an orbital reciprocal shaking platform (120 rpm) at 36.5° C. for 3 days. Samples were then removed and cell concentration was determined by haemocytometry.

Results

Figure 2A:
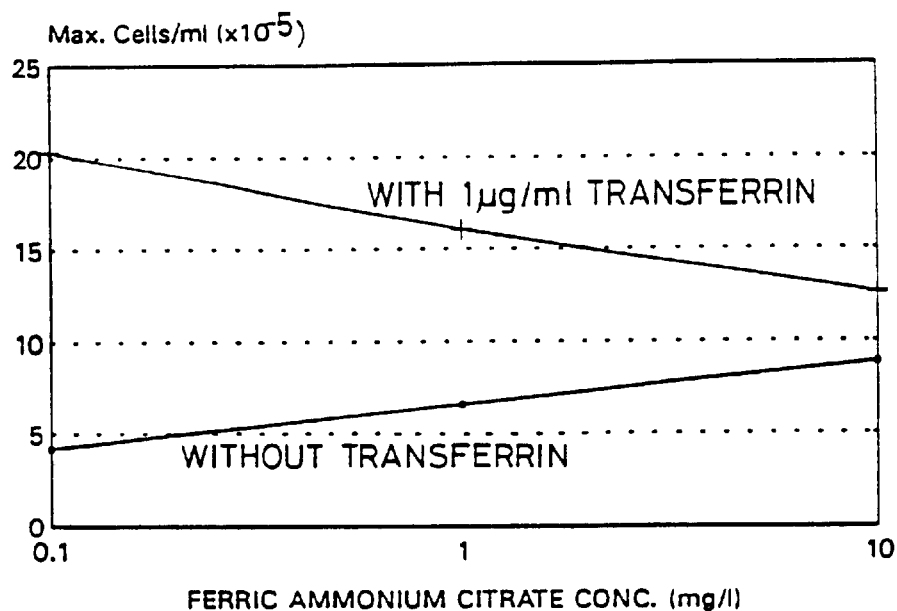
Figure 2B:
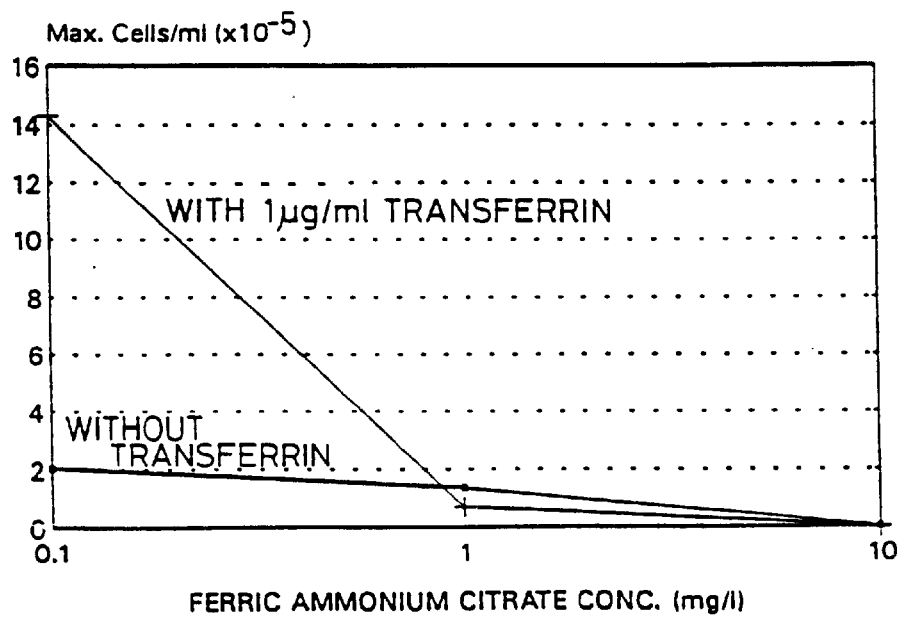

FIG. 2A shows that increasing concentrations of ferric ammonium citrate up to 10 mg/l support increasing cell concentrations in transferrin-free medium in static culture. However, FIG. 2B demonstrates that in agitated culture (reciprocal shaking platform) that ferric ammonium citrate concentrations of >1 mg/l are toxic in both the presence or absence of transferrin.

EXAMPLE 3

Figure 3A:
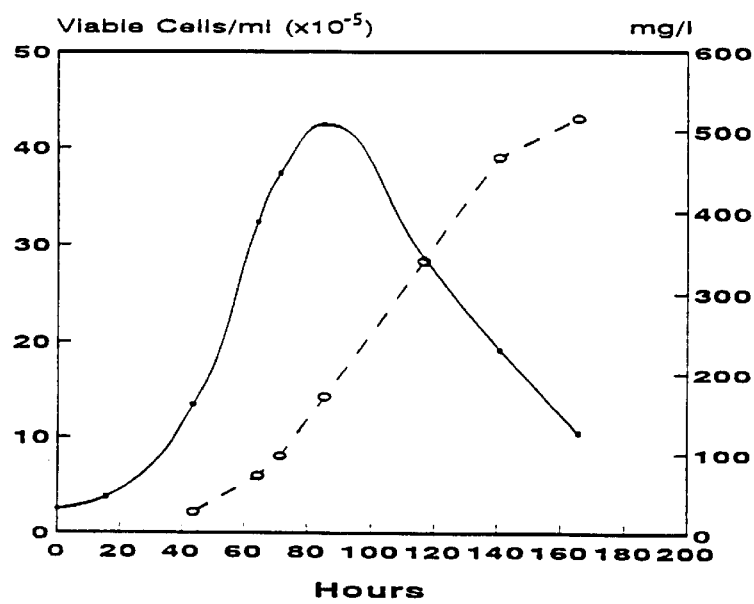

A mouse hybridoma cell line was subcultured in a proprietary serum-free medium containing 1 mg/l human transferrin and 0.01 mg/l ferric ammonium citrate (FIG. 3b), or a proprietary protein-free medium containing 5 μM tropolone and 0.1 mg/l ferric ammonium citrate (FIG. 3a). Agitated, sparged fed-batch fermentations of the cell line in each medium were carried out.

Figure 3B:
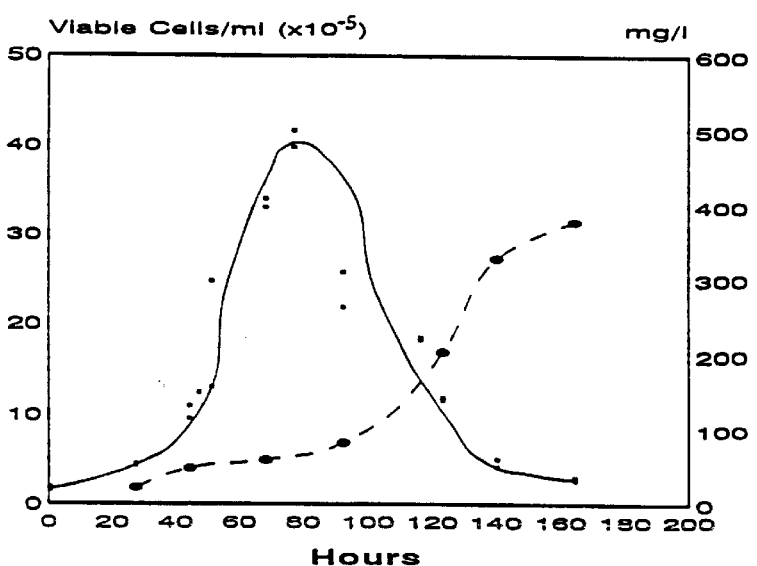

FIG. 3a and FIG. 3b demonstrate that similar cell growth and production characteristics are seen using either tropolone (FIG. 3a) or transferrin (FIG. 3b) in an agitated, sparged fermenter system.

EXAMPLE 4

A mouse hybridoma cell line was subcultured in transferrin-free medium containing 0.1 mg/l ferric ammonium citrate and 5 μM tropolone. Cells were centrifuged and resuspended in medium containing 0.01 mg/l ferric ammonium citrate and 5 μM tropolone at a density of $1.5 \times 10^5$ cells/ml in T-25 flasks. Extra ferric ammonium citrate was added to flasks to create a concentration range from 0.01–2 mg/l. Flasks were gassed with an atmosphere of 5% $CO_2$—95% air and incubated on an orbital shaking platform (120 rpm) at 36.5° C. for 3 days.

After 3 days samples were withdrawn from flasks and cell concentration determined using a Coulter multisizer.

Results

Figure 4:
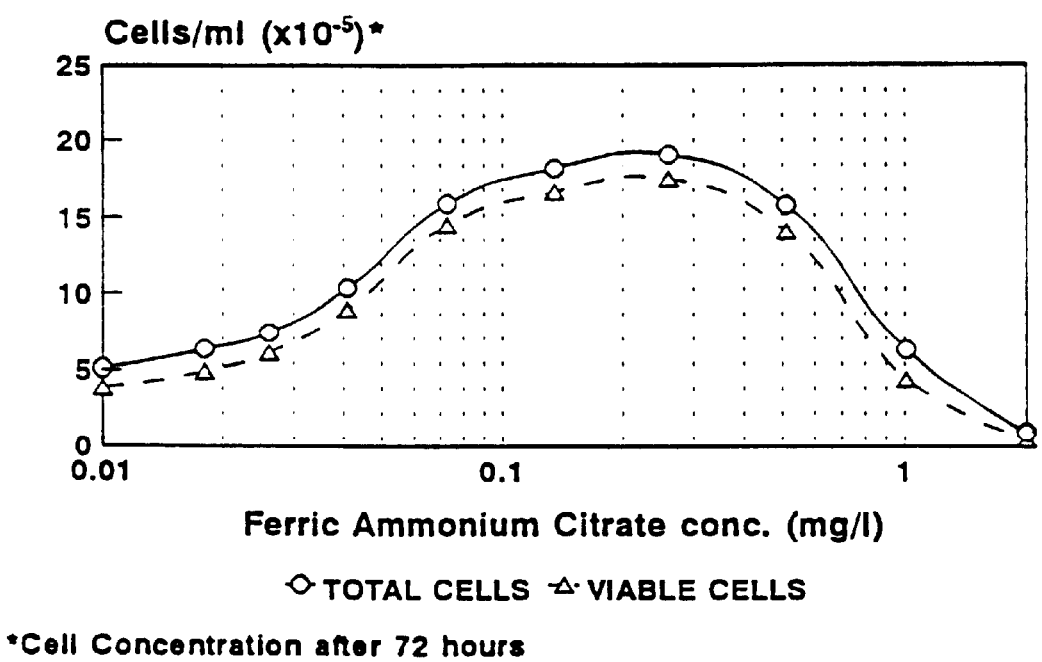

The cell concentration after 3 days growth is a combined function of iron concentration, cell growth rate and maximum biomass. Hence although maximum biomass is obtained in the range 0.075–1 mg/l ferric ammonium citrate (growth yield is $3.3 \times 10^7$ cells/μg ferric ammonium citrate—data not shown), maximum growth rate FIG. 4) is seen at 0.15×0.5 mg/l ferric ammonium citrate.

EXAMPLE 5

The efficacy of using tropolone as a transferrin replacement was further investigated using recombinant GS-myeloma cell lines [mouse NS/O] expressing humanised antibodies using the glutamine synthetase (GS) expression system, [Bebbington et al., Bio/Technology, 10, 169–175; European Patent Specification No. 256055]. Three recombinant cell lines producing different antibodies were grown in suspension culture in media containing 0.2 mg/l ferric ammonium citrate and either 5 μM tropolone or 1 mg/l transferrin. The growth rates were similar in either medium as was the peak viable cell concentration. For all three cell lines the antibody concentration at the end of the profile was similar when transferrin was replaced by tropolone (see Table 1). In the absence of either tropolone or transferrin but in the presence of 0.2 mg/l ferric ammonium citrate myeloma cells failed to thrive and died within 48 hours.

TABLE 1

| | Growth and Productivity of NSO Cell Lines in Medium Containing Tropolone | | | |
| --- | --- | --- | --- | --- |
| | TRANSFERRIN | | TROPOLONE | |
| | PEAK CELL DENSITY ($\times 10^6$/ml) | ANTIBODY TITRE (mg/l) | PEAK CELL DENSITY ($\times 10^6$/ml) | ANTIBODY TITRE (mg/l) |
| Cell line A | 1.30 | 438 | 1.51 | 420 |
| Cell line B | 1.46 | 301 | 1.49 | 241 |
| Cell line C | 2.62 | 29 | 3.17 | 32 |

EXAMPLE 6

A mouse myeloma cell line [GS-NSO, see Example 5] was subcultured in a transferrin-free medium containing 0.2 mg/l ferric ammonium citrate and 5 μM tropolone. Cells were centrifuged and resuspended in a protein-free medium [LS1] containing 0.2 mg/l ferric ammonium citrate and 5 μM tropolone at a density of $2 \times 10^5$ cells/ml in shake flasks. Flasks were gassed with an atmosphere of 5% $CO_2$—95% air and incubated on an orbital shaking platform (120 rpm) at 36.5° C.

Figure 5:
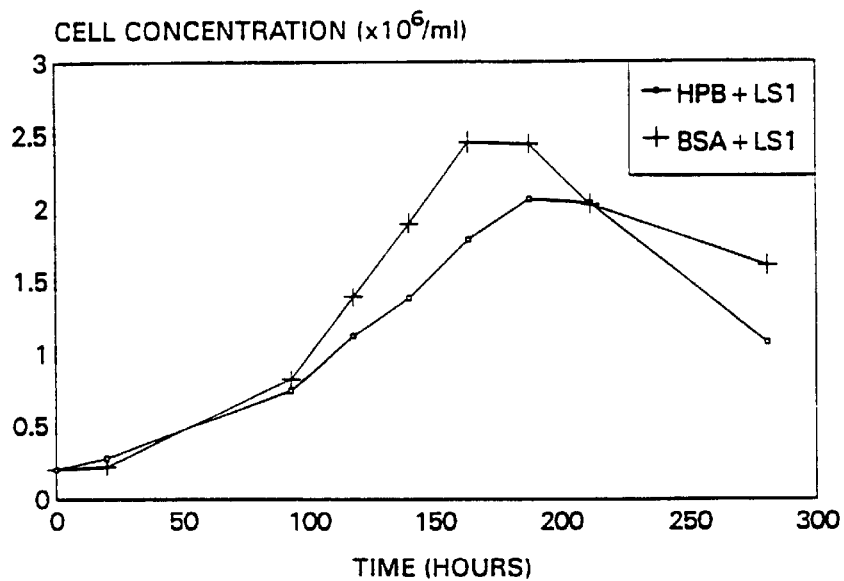
FIGS. 5 and 6 show the growth of mouse NS/O cells in the presence of tropolone.

FIG. 5 shows the resulting cell growth.

The LS1 medium additionally contained 2-hydroxypropyl-β-cyclodextrin [HPB; 1.2 g/l] complexed with cholesterol and fatty acids [prepared before addition to LS1 by dissolving HPB (0.6 mg/l) in water and adding to an equal volume of a supplement containing cholesterol and the fatty acids previously dissolved in absolute alcohol, then agitating for 3 hours prior to centrifugation and filtering]. As a control the same cells were grown in LS1 medium supplemented with cholesterol and fatty acids and containing 0.2 mg/l ferric ammonium citrate and 5 µM tropolone but using bovine serum albumin [BSA] in place of the HPB. FIG. 5 shows that tropolone is able to support the growth of both cultures and also that 2-hydroxypropyl-β-cyclodextrin is an effective replacement for bovine serum albumin as a carrier for cholesterol and fatty acids.

Figure 6:
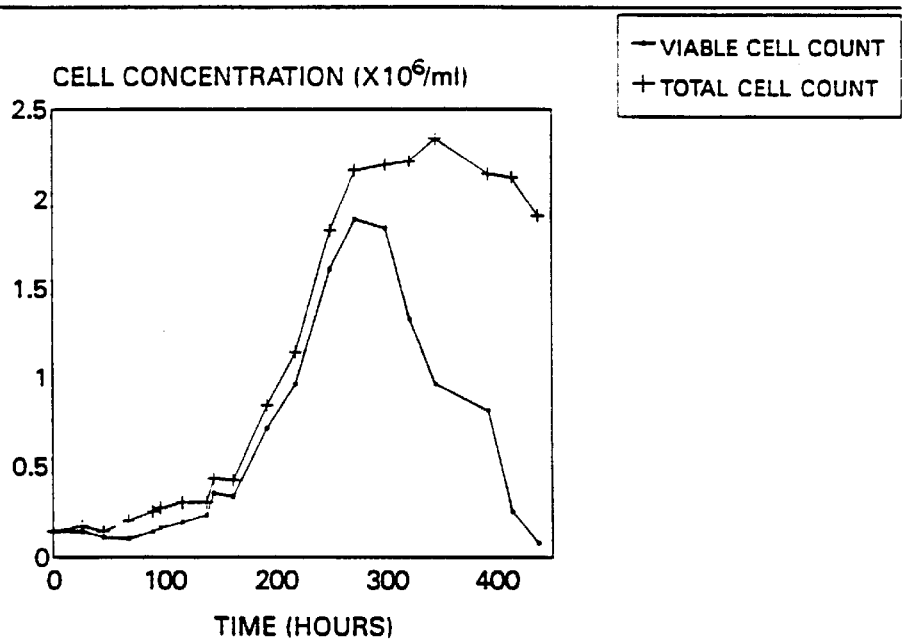

FIG. 6 shows the growth of the same myeloma cell line in a 5 L airlift fermenter using LS1 medium containing 0.2 mg/l ferric ammonium citrate and 5 µM tropolone.

What is claimed is:

1. A protein free nutrient animal cell culture medium comprising at least one assimilable source of each of the following:
   a) carbon,
   b) nitrogen,
   c) amino acids,
   d) iron and other inorganic ions, and
   e) trace elements,
in admixture with 2-hydroxy-2,4,6-cycloheptatrien-1-one or a derivative thereof.

2. A medium according to claim 1 wherein the 2-hydroxy-2,4,6-cycloheptatrien-1-one or derivative thereof is present in an excess molar concentration to the iron present.

3. A medium according to claim 2 wherein the 2-hydroxy-2,4,6-cycloheptatrien-1-one or derivative thereof and iron are present at a molar ratio of around 5 to 1 to around 70 to 1.

4. A medium according to claim 3 for the continuous growth of animal cells.

5. A medium according to claim 2 for the continuous growth of animal cells.

6. A medium according to claim 1 for the continuous growth of animal cells.

7. A medium according to claim 6 wherein the animal cell is a mammalian cell.

8. A medium according to claim 7 wherein the mammalian cell is a lymphoid cell.

9. A medium according to claim 8 wherein the lymphoid cell is a myeloma cell.

10. A medium according to claim 1, wherein the medium further comprises lipids and growth promoters or regulators.

11. A method for producing an animal cell product comprising:
   (a) culturing animal cells which produce said product in the nutrient medium of claim 1 until said product accumulates; and
   (b) recovering said product.

12. A method according to claim 11, wherein the medium comprises 2-hydroxy-2,4,6-cycloheptatrien-1-one or derivative thereof in an excess molar concentration to the iron present.

13. A method according to claim 12, wherein the 2-hydroxy-2,4,6-cycloheptatrien-1-one or derivative thereof and iron are present at a molar ratio of around 5 to 1 to around 70 to 1.

14. A method according to claim 11, wherein the animal cell is a myeloma cell.

* * * * *